US005721023A

United States Patent [19]
Ostapchenko

[11] Patent Number: 5,721,023
[45] Date of Patent: Feb. 24, 1998

[54] POLYETHYLENE TEREPHTHALATE ARTICLES HAVING DESIRABLE ADHESION AND NON-BLOCKING CHARACTERISTICS, AND A PREPARATIVE PROCESS THEREFOR

[75] Inventor: George Joseph Ostapchenko, Wilmington, Del.

[73] Assignee: E. I. du Pont de Nemours and Company, Wilmington, Del.

[21] Appl. No.: 460,290

[22] Filed: Jun. 2, 1995

Related U.S. Application Data

[62] Division of Ser. No. 169,448, Dec. 17, 1993, abandoned.

[51] Int. Cl.$^6$ .............................. B32B 5/16; B29D 22/00
[52] U.S. Cl. .................. 428/35.2; 428/35.5; 428/331; 428/409; 428/480; 604/96; 604/104
[58] Field of Search ........................ 428/331, 480, 428/409, 35.2, 35.5; 604/96, 104

[56] References Cited

U.S. PATENT DOCUMENTS

| Re. 33,561 | 3/1991 | Levy | 428/36.92 |
|---|---|---|---|
| 2,465,319 | 3/1949 | Whinfield et al. | 260/75 |
| 2,823,421 | 2/1958 | Scarlett | 18/57 |
| 3,153,683 | 10/1964 | Bryan et al. | 264/80 |
| 3,431,135 | 3/1969 | Keane et al. | 117/46 |
| 4,325,850 | 4/1982 | Mueller | 524/228 |
| 4,590,119 | 5/1986 | Kawakami et al. | 428/216 |
| 4,818,581 | 4/1989 | Katoh et al. | 428/143 |
| 5,137,939 | 8/1992 | Siddiqui | 523/219 |
| 5,215,825 | 6/1993 | Hiraoka et al. | 428/480 |
| 5,258,353 | 11/1993 | Macdonald et al. | 503/227 |
| 5,264,260 | 11/1993 | Saab | 428/35.5 |
| 5,318,833 | 6/1994 | Fujimoto et al. | 428/304.4 |
| 5,328,755 | 7/1994 | Mills et al. | 428/215 |
| 5,330,428 | 7/1994 | Wang et al. | 604/96 |

FOREIGN PATENT DOCUMENTS

| 0 261 460 | 3/1988 | European Pat. Off. | C08K 3/36 |
|---|---|---|---|
| 0 506 033 | 9/1992 | European Pat. Off. | C08K 3/36 |
| 288162 | 3/1991 | Germany | C08J 03/20 |
| 53 125479 | 11/1978 | Japan | B29D 07/24 |
| 54 150442 | 11/1979 | Japan | C09J 07/02 |
| 59 111849 | 6/1984 | Japan | B32B 27/36 |
| 59 206456 | 11/1984 | Japan | C08L 67/02 |
| 02 127022 | 5/1990 | Japan | B29C 47/88 |
| 02 203422 | 8/1990 | Japan | G11B 05/78 |
| 03 207651 | 9/1991 | Japan | B29C 55/12 |
| 04 341840 | 11/1992 | Japan | B32B 27/20 |
| 04 341841 | 11/1992 | Japan | B32B 27/20 |
| 05 124100 | 5/1993 | Japan | B29C 55/12 |

OTHER PUBLICATIONS

R.E. Johnson, et al., Surface and Celloid Science, *Interscience*, New York, NY, 2, 86–153, 1969.

D.K. Owens, The Mechanism of Corona and Ultraviolet Light Induced Self–Adhesion of Poly(ethyleneterephthalate) Film, *J. Applied Sci.*, 19, 3315–3326, 1975.

R.K. Iler, *The Chemistry of Silica*, John Wiley & SOns, Inc., 428–429; 578; 587; 1979.

G.J.L. Griffin, *Appl. Polym. Symp.*, 16, 67–86, 1971.

D.K. Owens, "Mechanism of Corona–Induced Self–Adhesion of Polyethylene Film", *J. Applied Poly. Sci.*, 19, 265–271, 1975.

P.W. Rose et al., Plasma Treatment, *Plastics Finishing and Decoration*, Van Nostrand Reinhold Company, pp. 90–100, 1986.

*Primary Examiner*—H. Thi Le

[57] ABSTRACT

Surface treated articles of polyethylene terephthalate (PET) are disclosed having low self-adhesion and high bondability to other surfaces. The articles comprise oriented PET and about 100–5000 ppm of a particulate additive uniformly dispersed therein. The additive is chemically inert to PET and has an average particle size of about 0.03 to 0.6 micrometers. A process for the preparation of such articles is also disclosed.

9 Claims, No Drawings

POLYETHYLENE TEREPHTHALATE ARTICLES HAVING DESIRABLE ADHESION AND NON-BLOCKING CHARACTERISTICS, AND A PREPARATIVE PROCESS THEREFOR

This is a division of application Ser. No. 08/169,448, filed Dec. 17, 1993, now abandoned.

BACKGROUND OF THE INVENTION

Polyethylene terephthalate (PET) has been demonstrated as an effective polymer for a wide variety of products. Its properties of strength, durability and the like make it suitable for any number of applications, from filaments and fibers to beverage containers.

Many uses of polyethylene terephthalate are derived from the film form. Films are prepared by many techniques well known to the practitioner, including extrusion.

Moreover, if the polyethylene terephthalate film is molecularly oriented, certain physical properties such as tensile strength, impact strength, flex life, and permeability to water and organic vapors are enhanced.

Oriented polyethylene terephthalate is widely used in a variety of industries including electronics (as dielectrics, coverings, and the like), the wire and cable industry (as, for example, filaments and protective sheaths), fibers, and polymeric articles of manufacture (such as beverage containers), to name a few. It finds particular application in the medical device field, including medical dilatation products where strength is a critical property. For example, U.S. Re 33,561 relates to medical dilation balloons (balloon catheters) especially useful in medical dilatation procedures.

One limitation to oriented polyethylene terephthalate film is that it is difficult to adhesively bond to other polymeric substrates. Such adhesion is desirable as with Re 33,561 inasmuch as the polymeric balloon must be suitably attached to other medical instruments for insertion into a vessel and surgical manipulation. The surface adhesion properties of oriented polyethylene terephthalate film are improved when it is subjected to surface treatment with, for example, any of the following energy sources: electrical stress accompanied by corona discharge; a flame; a gaseous plasma (such as oxygen, chlorine, etc.); short wave ultraviolet light; and oxidizing chemicals (sulfuric acid dichromate, potassium permanganate, etc.). The treated surface is generally characterized by measuring the contact angle between a drop of liquid (usually water) and the treated surface, according to conventional techniques. For example, the Sessile drop technique as reviewed by R. E. Johnson, Jr. and R. H. Dettre, "Surface and Colloid Science", Volume 2, Interscience, New York, N.Y., 1969 measures advancing and receding contact angles for two chemicals at a given temperature. High contact angle values indicate a low concentration of polar groups (or less adhesion) and low values indicate a high concentration of polar groups (or more adhesion).

However, a consequence of such surface treatment procedures is that while adhesion of the oriented polyethylene terephthalate film to other materials improves, the film undesirably adheres to itself when two such treated surfaces contact one another. This self-adhesion phenomenon, known as blocking, can occur, for example, when films are stacked for storage, when folds of dilation balloons are tightly wrapped together, or when filaments are pinched together. Blocking tendency is enhanced under high humidity conditions and moderate pressure during storage.

Blocking is also known to occur in oriented polyethylene terephthalate articles that have not been surface treated, but only under extremes of temperature and pressure. Any treatment that enhances adhesion to other materials may also contribute sharply to blocking. Blocking can be so severe that when the surfaces are pulled apart, damage is sufficient to render the article unusable.

D. K. Owens, J. Applied Polymer Sci., 19, 3315 (1975) showed that oriented polyethylene terephthalate film after corona or ultraviolet radiation treatment exhibits strong self-adhesion under bonding conditions where no adhesion occurs with untreated film. Self-adhesion was shown to be reversibly reduced by the application of hydrogen-bonding liquids to the film surface, or by chemical reaction of the polar groups present on the radiation-treated surface.

R. K. Iler, in "The Chemistry of Silica", John Wiley & Sons, Inc., 1979, pp. 428, 429, 578, 587, discloses that colloidel silica, silica gels or silica powders incorporated with polymers can reduce self-adhesion or blocking of the polymer. Small particles of silica on the surface of a polyester film are said to act as spacers, preventing sticking and blocking. Antiblocking in polymer films can be attained by adding fine particulate silica to the mixed monomers before polymerization; 0.5% silica, based on polymer, allegedly reduces self-adhesion by 50%.

Japanese Application 59 206456 (11/1984); CA 102 (16) :133192k discloses block-resistant oriented polyester films having excellent adhesion to vapor-deposited metals, prepared by polymerizing ethylene glycol and terephthalic acid in the presence of 10–10,000 ppm of powdered kaolinite having a particle size of 0.1–3 micrometers. The resultant polymer was then mixed with 50–20,000 ppm of a fatty amide, melt extruded, cast and biaxially stretched into film.

Japanese Application 53 125479 (11/1978); discloses biaxially oriented polyester films containing 80 ppm silica having an average particle diameter of 0.3 micrometer and 20 ppm of kaolin having an average particle diameter of 0.8 micrometer, said films having a peak-to-valley surface roughness of 0.05–0.3 micrometer and excellent block resistance.

G. J. L. Griffin, Appl. Polym. Symp., No. 16, 1971 67–86; discloses that the incorporation of particulate silica antiblocking additive into low density polyethylene extruded film produces numerous small protuberances in the film surface and that the polymer has lower solubility in the regions of the protuberances.

It remains a desirable goal to provide an oriented polyester film that not only exhibits strong antiblocking characteristics, but can also be strongly bonded to the surfaces of other materials.

SUMMARY OF THE INVENTION

The present invention provides a surface-treated article of oriented polyethylene terephthalate (PET) exhibiting low self-adhesion and high bondability to other surfaces, consisting essentially of oriented PET and about 100 to about 5000 parts per million (ppm) of a particulate additive uniformly dispersed therein, the additive being chemically inert to PET and having an average particle size in the range of about 0.03 to about 0.6 micrometers.

Also provided is a process for preparing an article of oriented polyethylene terephthalate exhibiting low self-adhesion and high bondability to other surfaces, comprising:
  (a) admixing with a polymerization solution comprising an alkyl ester of terephthalic acid and ethylene glycol a particulate additive uniformly dispersed in ethylene glycol, the additive being chemically inert under polymerization conditions and having an average particle size in the range of about 0.03 to about 0.6 micrometers, in an amount sufficient to provide a particulate additive content in the polymerization product in the range of about 100 ppm to about 5000 ppm;

(b) polymerizing the mixture of step (a) and subsequently isolating a PET/particulate additive product therefrom;

(c) forming an oriented article of the product of step (b); and (d) treating a surface of the oriented article with an energy source to increase the polarity of the surface.

The surface-treated, oriented PET article of the invention has increased surface polarity relative to untreated oriented PET and exhibits high bondability to other surfaces. The article nevertheless exhibits low self-adhesion or blocking relative to a surface-treated, oriented PET article containing no particlulate additive.

Many different articles of manufacture are contemplated for preparation according to the process of the invention. Films and tubes may be prepared by this process, of various sizes and shapes as required by the practitioner. In the field of medical devices, medical dilation balloons are advantageously prepared according to Re 33,561, previously referenced, using surface-treated, oriented polyethylene terephthalate film of the present invention.

DETAILED DESCRIPTION OF THE INVENTION

Polyethylene terephthalate is prepared by numerous methods; one such method is according to U.S. Pat. No. 2,465,319 which is incorporated by reference herein. In general, this preparation involves the condensation of ethylene glycol and terphthalic acid. The resulting product in the from of a film is next stretched in longitudinal and transverse directions in a manner such as is described in U.S. Pat. No. 2,823,421 (incorporated by reference herein) to provide a biaxially oriented polyethylene terephthalate film. U.S. Pat. No. 2,823,421 is directed to the stretching of polyethylene terephthalate film to produce an oriented product having an outstanding combination of physical, chemical and electrical properties. An extruded, molten amorphous film of polyethylene terephthalate is continuously longitudinally stretched at a rate of at least 400 percent per minute for not more than 3.25 times at a temperature of 80°–90° C. The longitudinally stretched film is then preheated at 90°–95° C. and continuously transversely stretched substantially the same amount and at the same rate at a temperature of 90°–110° C., to produce a balanced, biaxially oriented film. The film is finally heat-set at 150°–250° C.

In the surface treatment step (d), "surface" is any of the surfaces of the article for which enhanced properties according to this invention is desired. It may be one side of the article or, for example, the inside and outside of a dilation balloon. The "energy source" employed in the surface treatment step (d) may be selected from a wide variety of conventional energy sources used for surface treatment techniques, including, without limitation, electrical stress accompanied by corona discharge; plasma; flame; ultraviolet light; and chemical treatment.

Treatment with corona discharge or ultraviolet light can be conducted according to the procedures set forth in Owens, D. K., "The Mechanism of Corona and Ultraviolet Light Induced Self-Adhesion of Poly(ethylene terephthalate) Film", J. Applied Poly. Sci., 19, 3315–3326 (1975). Corona treatment is also described in Owens, D. K., "The Mechanism of Corona and Ultraviolet Light Induced Self-Adhesion of Poly(ethylene terephthalate) Film", J. Applied Poly. Sci., 19, 265–271 (1975).

A discussion of surface treatment using plasma appears in Rose, P. W. and Kaplon, S. L. "Plasma Treatment", Plastics Fishing and Decoration, Van Nostrand Reinhold Company, 1986. Preferably, surface treatment using plasma is conducted for less than about 16 minutes and at less than 300 watts. U.S. Pat. No. 3,431,135 and U.S. Pat. No. 3,153,683 review the fundamentals of flame treatment. Any of a variety of chemicals may be used for their surface treating properties. Such chemicals are selected according to the desired result, as will be readily appreciated by those skilled in the art.

With respect to the particulate additive present in the PET of the invention, said additive must be uniformly dispersed within the PET, must be chemically inert towards PET, and have an average particle size in the range of about 0.03 to about 0.6 micrometer, preferably 0.06 to 0.3 micrometer. The particles are preferably but not essentially spherical in shape.

The particulate additive should be present in the PET of the invention at a concentration in the range of about 100 to about 5000 parts per million (ppm), preferably 500 to 2000 ppm.

The amount, particle size and particle shape of the particulate additive used in the present process is important not only for the control of self-adhesion in the matrix PET but also for retaining the strength of films and other articles prepared by the process. Of particular interest herein is the preparation of medical dilation balloons wherein balloon burst strength as well as adhesive properties is particularly important.

A preferred particulate additive is silica. Other particulate compounds may be used, however, provided they are of the required particle size and are chemically inert to PET, both under in-use conditions and under conditions of preparation of the PET articles of the invention.

In step (a) of the present process for preparing articles of the invention, the particulate additive is uniformly dispersed within the PET by admixing a dispersion of said additive in ethylene glycol with a polymerization solution of ethylene glycol and an alkyl ester of terephthalic acid, preferably the methyl ester, and then polymerizing said solution in the presence of the additive according to known condensation polymerization methods, such as those described in the references described hereinabove. Appropriate additives will be stable and inert under said polymerization conditions. Sufficient additive dispersion is admixed with the glycol and diester monomers to provide a particulate additive content in the final polymerization product in the range of about 100 ppm to about 5000 ppm, preferably 500 to 2000 ppm.

In the process of the invention, sequential steps (a) and (b) are essential for obtaining a uniform dispersion of particulate additive in the polymer. Post-polymerization addition of particulates to polymer does not provide adequately uniform distribution of particles within the polymer for purposes of this invention. The present process is also believed to result in the complete encapsulation of the additive particles within the polymer, so that no free additive is present in the surface of the final polymeric article.

U.S. Re 33,561 which is incorporated by reference herein provides for balloon catheters useful for the relief of arterial stenosis and other ailments requiring a surgical procedure involving insertion of an instrument into blood vessels or body cavities. These balloons are effective in that they have thin walls which are flexible, readily collapsible and easily transportable within the body. Other physical properties include minimal radial expansion on inflation, and high burst strength (with any rupture confined to the axial direction to ensure against traumatic removal), among other attributes making these balloons effective for a number of medical procedures. The patent requires that the flexible balloon be made of a high molecular weight, biaxially oriented polymer having a burst pressure of at least 200 psi (1.4 MPa) and a radial expansion of less than 5 percent at 200 psi (1.4 MPa).

In experiments with medical dilation balloon catheters, it has been found that adequate adhesion of the surface treated, oriented polyethylene terephthalate articles of the invention to other surfaces, particularly polymeric surfaces such as polyethylene, requires use of an adhesive. Suitable adhesives are commercially available products such as, for example, ultraviolet light-curable acrylic adhesives. Such adhesives are well known to those skilled in the art. Destructive testing of dilation balloon catheters has shown that adhesive bonding of surface treated, oriented polyethylene terephthalate directly to polyethylene without use of an adhesive, or adhesive bonding of untreated, oriented polyethylene terephthalate to polyethylene with an adhesive, each results in bond failure rather than balloon failure. Use of an adhesive in bonding surface treated balloons of the present invention to polyethylene results in balloon failure rather than bond failure in destructive testing; balloon failure is the desired mode of failure.

It has also been observed that protective coatings, such as, for example, silicone coatings, applied to the outer surface of dilation balloons for improved abrasion resistance, adhere adequately to the surface treated, oriented polyethylene terephthalate balloons of this invention but not to untreated, oriented polyethylene terephthalate balloons.

The presence of particulate additive in the articles of the present invention provides anti-blocking properties without in any way impairing bondability of said articles to other surfaces.

Although numerous applications are envisaged for PET oriented, surface-treated articles of the invention that are at once relatively non-blocking yet adherable to other surfaces, the following specific embodiments relate to medical dilation balloons. However, it will be clear to those of ordinary skill in the art that the non-blocking and adhesive properties demonstrated for the dilation balloons can be achieved with oriented PET articles prepared for different uses by the process of the invention.

EXAMPLES

PROCEDURE

The following illustrates the general procedure used in the examples of the invention, except that no particulate additive was present. The results of this procedure section provide a basis of comparison for the examples wherein particulate additive is present.

Polyethylene terephthalate (PET) resin having an intrinsic viscosity of about 1, a density of 1.41 g/cm$^3$, and a diethylene glycol content of about 2 weight percent, was dried to less than 0.005 weight percent water at 177° C. and then processed into single lumen tubing having an outside diameter of 0.34 mm and a wall thickness of 0.064 mm, using conventional tubing extrusion technique. Biaxially oriented balloons having an outside diameter of 3 mm, a single wall thickness of 0.0076 mm and a cylindrical length of 2 cm were fabricated from the extruded tubing using the process of U.S. Pat. No. Re 33,561, and then plasma treated in an oxygen atmosphere maintained at a pressure between 13 and 130 Pa in a Gasonics/IPC Model 7102 Plasma Treater for 8 minutes at 300 watts and 13.56 MHz.

Twenty balloons were tested for burst pressure by measuring the balloon pressure at which failure occurred, resulting in an average value of 1937 KPa with a standard deviation of 71 KPa.

Ten plasma-treated balloons were tested for blocking by connecting the proximal end of a balloon to a Tuohy-Borst adapter and then heat sealing the distal end with an electrical heating element. The Tuohy-Borst adapter with the sealed balloon attached was then connected to a commercial "PRESTO" inflation device (C. R. Bard, Inc. USC Division), that had been deaerated as much as possible and contained 4 cm$^3$ of distilled water. With the inflation device pointed down, the plunger was pulled to its limit to remove air from the balloon; the balloon was evacuated to a pressure of about 16 KPa. With the balloon evacuated, the screw plunger was pushed and rotated to achieve a pressure of 1300 KPa. This pressure was held for one minute while the balloon was checked for leaks. If no leaks were found, the plunger was pulled to its limit, again with the pressure device pointing down, to achieve a balloon pressure of about 16 KPa. While ensuring that the balloon had been completely deflated, this pressure was held for 20 minutes.

The balloon was then reinflated to a pressure of 1200 KPa as quickly as possible and maintained at that pressure for one minute while the balloon was checked for leaks. The balloon pressure was returned to atmospheric and the Tuohy-Borst adapter and balloon were disconnected from the inflation device. The inside surface of the balloon was then examined for delamination caused by blocking, using a stereo polarizing microscope. Changes in balloon wall thickness as a result of delamination were evident as localized differences in retardation colors when viewed between crossed Polaroid's (step A).

If blocking was not observed, the Tuohy-Borst adapter with balloon was reattached to the inflation device and the vacuum-pressure-vacuum cycle was repeated except that the final vacuum was held for 40 minutes. The balloon was again checked for leaks at 1200 KPa and re-inspected for delamination using the stereo polarizing microscope (step B). If blocking was not observed, the vacuum-pressure-vacuum cycle was again repeated except that the final vacuum was held for 140 minutes. The balloons were again checked for leaks and delamination (step C).

All ten balloons passed step A. Six balloons failed at step B, and the remaining four balloons failed at step C.

A Blocking Tendency value was obtained by assigning a value of 10 (100 divided by the number of balloons tested) to balloons that failed at step A, 5 (50 divided by the number of balloons tested) to balloons that failed at step B and 1 (10 divided by the number of balloons tested) to balloons that failed at step C. A Blocking Tendency value of 100 indicates all balloons failed at step A, and a value of 0 indicates that all balloons survived all three steps. A Blocking Tendency value of 34 (6 balloons×5 plus 4 balloons×1=34) was obtained.

Example 1

Balloons were fabricated using a PET resin having essentially the same properties as in the results of the Procedure section, except the resin contained 1230 ppm of spherical silica particles having an average particle size of 0.3 micrometer. The silica particles were added as a slurry in ethylene glycol (Nippon Shokubai "Seahostar" KE-E30) to the mixture of ethylene glycol and dimethyl terephthalate monomers before polymerization. The average burst strength of 20 balloons was 2014 KPa with a standard deviation of 88 KPa. The Blocking Tendency value for 10 plasma-treated balloons was 0.

Example 2

Balloons were fabricated using a PET resin having essentially the same properties as in the results of the Procedure section, except that the resin contained 825 ppm of spherical silica particles having an average particle size of 0.3 micrometer. The silica particles were added as a slurry in ethylene glycol (Nippon Shokubai "Seahostar" KE-E30) to the mixture of ethylene glycol and dimethyl terephthalate monomers before polymerization. The average burst strength of 20 balloons was 2068 KPa with a standard deviation of 73 KPa. The Blocking Tendency value for 10 plasma treated balloons was 1.

Example 3

Balloons were fabricated using a PET resin having essentially the same properties as in the results of the Procedure section, except that the resin contained 545 ppm of spherical silica particles having an average particle size of 0.2 micrometer. The silica particles were added as a slurry in ethylene glycol (Nippon Shokubai "Seahostar" KE-E20) to the mixture of ethylene glycol and dimethyl terephthalate monomers before polymerization. The average burst strength of 20 balloons was 2093 KPa with a standard deviation of 79 KPa. The Blocking Tendency value for 10 plasma treated balloons was 1.

Example 4

Balloons were fabricated using a PET resin having essentially the same properties as in the results of the Procedure section, except that the resin contained 920 ppm of spherical silica particles having an average particle size of 0.2 micrometer. The silica particles were added as a slurry in ethylene glycol (Nippon Shokubai "Seahostar" KE-E20) to the mixture of ethylene glycol and dimethyl terephthalate monomers before polymerization. The average burst strength of 20 balloons was 1937 KPa with a standard deviation of 71KPa. The Blocking Tendency value for 10 plasma treated balloons was 4.

Example 5

Balloons were fabricated using a PET resin having essentially the same properties as in the results of the Procedure section, except that the resin contained 1554 ppm of spherical silica particles having an average particle size of 0.06 micrometers. The silica particles were added as a slurry in ethylene glycol (Philadelphia Quartz Co.'s Silica Dispersion DP5480) to the mixture of ethylene glycol and dimethyl terephthalate monomers before polymerization. The average burst strength of 20 balloons was 1937 KPa with a standard deviation of 71KPa. The Blocking Tendency value for 10 plasma treated balloons was 4.

I claim:

1. A balloon catheter of polyethylene terephthalate (PET) suitable for use in invasive medical procedures exhibiting a Blocking Tendency Value (BTV) of less than 10 and an adhesive bond with polyethylene of greater than 1.90 MPa, consisting essentially of a biaxially oriented PET catheter balloon containing about 500 to about 2000 parts per million (ppm) of particulate silica of an average particle size of about 0.06 to about 0.3 micrometers, and uniformly dispersed therein; and further wherein the balloon catheter is treated with an energy source to increase the polarity thereof.

2. A process for preparing a medical dilation catheter balloon of biaxially oriented polyethylene terephthalate (PET) exhibiting a Blocking Tendency Value (BTV) or less than 10 and an adhesive bond with polyethylene of greater than 1.9 MPa, comprising:

(a) admixing with a polymerization solution comprising an alkyl ester of terephthalic acid and ethylene glycol, a particulate additive uniformly dispersed in ethylene glycol, said additive being chemically inert under polymerization conditions and having an average particle size in the range of about 0.03 to about 0.6 micrometers, in an amount sufficient to provide a particulate additive content in the range of about 100 ppm to about 5000 ppm by weight of mixture formed thereby;

(b) polymerizing the mixture of step (a) and subsequently isolating a PET/particulate additive product therefrom;

(c) forming a biaxially oriented medical dilation catheter balloon of the product of step (b); and (d) treating a surface of said catheter balloon with an energy source to increase the polarity of said surface, wherein the energy source is selected from the group consisting of electrical stress accompanied by corona discharge, plasma, flame, ultraviolet light and chemical reaction.

3. The process according to claim 2 wherein the particulate additive is present in the range of 500 to 2000 ppm.

4. The process according to claim 2 wherein the average particle size of the particulate additive is in the range of 0.06 to 0.3 micrometers.

5. The process according to claim 2 wherein the particulate additive consists of particles which are essentially spherical.

6. The process according to claim 2 wherein the particulate additive is silica.

7. The process according to claim 2 wherein the energy source is plasma.

8. The process according to claim 7 wherein, in step (d), the surface is treated with plasma for less than about 16 minutes and at less than about 300 watts.

9. The medical dilation balloon according to claim 2 having a BTV of less than 5.

* * * * *